United States Patent [19]
Berggren et al.

[11] Patent Number: 5,323,789
[45] Date of Patent: Jun. 28, 1994

[54] ANASTOMOSIS PREPARATION TECHNIQUE WITH EASILY INSERTABLE MEMBER

[75] Inventors: Anders Berggren, Linkoping; Hakan Rohman, Mantorp; Rafn Ragnarsson, Linkoping, all of Sweden; Floyd L. Foslien, Hudson, Wis.

[73] Assignee: Minnesota Mining and Manufacturing Company, St. Paul, Minn.

[21] Appl. No.: 739,849

[22] Filed: Aug. 2, 1991

Related U.S. Application Data

[63] Continuation-in-part of Ser. No. 578,544, Sep. 6, 1990, Pat. No. 5,036,868, which is a continuation of Ser. No. 471,706, Jan. 29, 1990, abandoned, which is a continuation of Ser. No. 235,882, Aug. 18, 1988, abandoned.

[30] Foreign Application Priority Data

| Dec. 18, 1986 | [SE] | Sweden | 8605455-8 |
| Dec. 16, 1987 | [CA] | Canada | P-554448 |
| Jul. 4, 1988 | [EP] | European Pat. Off. | 88900479.2 |
| Aug. 12, 1988 | [DK] | Denmark | 4529/88 |
| Aug. 17, 1988 | [AU] | Australia | P-10836/88 |
| Aug. 17, 1988 | [BR] | Brazil | PI-8707589 |

[51] Int. Cl.⁵ .............................. A61B 17/00
[52] U.S. Cl. .............................. 128/898; 606/191; 606/192–198; 604/49; 604/104
[58] Field of Search .............. 606/191–194, 606/196, 198; 604/94–104; 128/898

[56] References Cited

U.S. PATENT DOCUMENTS

| 3,050,066 | 8/1962 | Koehn . | |
| 3,438,375 | 4/1969 | Ericson . | |
| 3,516,408 | 6/1970 | Montanti . | |
| 4,230,119 | 10/1980 | Blum . | |
| 4,447,227 | 5/1984 | Klotsanis | 604/95 |
| 4,523,592 | 6/1985 | Daniel | 606/153 |
| 4,547,187 | 10/1985 | Kelly | 604/49 |
| 4,607,637 | 8/1986 | Berggren et al. . | |
| 4,624,257 | 11/1986 | Berggren et al. . | |
| 4,733,665 | 3/1988 | Palmaz | 604/104 |
| 4,917,090 | 4/1990 | Berggren et al. | 606/153 |
| 4,917,091 | 4/1990 | Berggren et al. | 606/153 |
| 4,950,238 | 8/1990 | Sullivan | 604/22 |
| 5,036,868 | 8/1991 | Berggren et al. | 606/192 |

FOREIGN PATENT DOCUMENTS

| 10836/88 | 8/1988 | Australia . |
| 88/04539 | 6/1988 | PCT Int'l Appl. . |
| 8605455-8 | 9/1988 | Sweden . |

Primary Examiner—Stephen C. Pellegrino
Assistant Examiner—Gary Jackson
Attorney, Agent, or Firm—Gary L. Griswold; Walter N. Kim; Jeffrey J. Hohenshell

[57] ABSTRACT

The invention pertains to a method for expanding a vessel during a surgical procedure. The method utilizes a device comprising an expandable elastic portion and a flexible pipe portion. The pipe portion is situated at an angle relative to the elastic portion. The method includes the steps of cutting a stab incision in the vessel, inserting the expandable elastic portion into the vessel, and expanding the elastic portion.

6 Claims, 3 Drawing Sheets

ANASTOMOSIS PREPARATION TECHNIQUE WITH EASILY INSERTABLE MEMBER

CROSS REFERENCE TO RELATED APPLICATIONS

The present application is a continuation-in-part of U.S. Ser. No. 578,544, now U.S. Pat. No. 5,036,868 filed Sep. 5, 1990, and which is a continuation of U.S. Ser. No. 471,706, filed on Jan. 29, 1990, now abandoned, which in turn, is a continuation of U.S. Ser. No. 235,882, filed on Aug. 18, 1988, now abandoned, as a United States National Patent Application, which is a result of the completion of P.C.T. phase of P.C.T. Serial No. PCT/SE87/00596, filed on Dec. 11, 1987. The P.C.T. application claims priority based on Swedish patent application, Serial No. 8605455-8, filed on Dec. 18, 1986. Furthermore, all of these applications are incorporated herein by reference in their entirety.

1. Field of the Invention

This invention relates in general to anastomotic preparation techniques, and in particular, to a method and improved apparatus for minimizing constrictions in blood vessels at the site of branching during anastomotic ring placement.

2. Background of the Invention

In vessel surgery, it has become increasingly useful to use by-passes. For example, constricted vessels can be replaced by healthier ones that are coupled in parallel or connected to other vessel locations. Until now, vessels have been joined with a common technique of sewing the vessels together with sutures.

More recently, anastomosis rings have become available for joining blood vessels, for example, in end-to-end and end-to-side anastomosis. Examples of apparatuses and techniques used in anastomosis are disclosed in U.S. Pat. Nos. 4,607,637; 4,624,257; 4,917,090 and 4,917,091 to Berggren et al. the entire contents of which are herein incorporated by reference.

In end-to-side anastomosis, a small cut is punctured in a first blood vessel, which is then flared or everted and placed over the pins of an anastomosis ring. The flared joint can then be attached with a complementary anastomosis ring to the end of a second vessel. In this way, it is possible to conduct a branching or by-passing procedure in considerably less time than with conventional suturing techniques. The use of anastomosis rings, in this fashion, is known to diminish the risks to the patient and to conserve resources.

Regretfully, the use of anastomosis rings for end-to-side joining of blood vessels is not entirely without drawbacks. It has been found that the application of the anastomosis rings to a vessel steals material from the vessel and results in a constriction in its diameter. This is undesirable, since one of the objectives of a by-pass is to improve flow, and not to replace one impedance to flow with another. Accordingly, there is a need for a technique and instrument for eliminating constrictions caused by anastomotic ring placement.

The T-shaped member described in U.S. Pat. application Ser. No. 578,544, which is expected to Issue on Aug. 6, 1991 as U.S. Pat. No. 5,036,868, is used in anastomosis procedures which are directed to solving the above mentioned problems. However, such a T-shaped member is believed to be relatively difficult to insert into stab incisions in small vessels. After a leading end of the T-shaped member's upper part or "expander balloon" is inserted into the vessel as far as the hose will allow, the trailing end must be deformed and placed into the vessel. Such a procedure may be difficult to accomplish and it is likely that the hole formed in the side of the vessel could be inadvertently enlarged during the insertion of the trailing end of the upper part. It is known in the art that it is desirable to restrict expansion of the stab incision as such expansion tends to inhibit attachment of the vessel to the anastomosis ring.

SUMMARY OF THE INVENTION

In accordance with the present invention, an instrument and procedure utilizing that instrument have been developed for minimizing constrictions in a vessel in a joint area at the site of anastomotic ring placement. The procedure includes inserting an upper part of a hollow, T-shaped member through an incision in the vessel. The T-shaped member includes a vertical part comprising a pipe or hose and an upper part, which is more elastic than the vertical part, which consists essentially of an expansible elongated balloon in an unexpanded state. The elongated balloon is in open communication with the hollow vertical part. The method also includes pressurizing the hollow vertical part. The method also includes pressurizing the hollow portion of the upper part by forcing a pressure medium through the vertical part into the upper part so as to expand the upper part and thereby substantially uniformly deform a portion of the joint area of the vessel. After the vessel has been deformed, the upper part is depressurized by removing the pressure medium, which allows the upper part to return to its unexpanded state. The upper part of the T-shaped member is then removed from the vessel prior to attachment of an anastomotic ring.

Accordingly, constrictions are minimized in the vessel and a more successful by-pass or branching operation can be performed. It is believed that the surgical instrument of this invention can provide additional surface area of vessel material for attachment of the anastomotic ring, thereby avoiding a reduction in diameter of the vessel during the surgical procedure.

A second embodiment of the present invention utilizes an improved, easily insertable instrument and a procedure that uses the improved instrument for minimizing constrictions in a vessel in a joint area at the site of anastomotic ring placement. The instrument according to the second embodiment of the present invention comprises (1) an expandable elastic portion having a middle part, leading and trailing closed ends and a longitudinal axis passing through the leading and trailing ends, and (2) a flexible pipe portion joined to and in open communication with the elastic portion generally at the middle part. The pipe portion has a longitudinal axis forming an acute angle with a portion of the longitudinal axis of the expandable elastic portion that passes through the trailing end of the expandable elastic portion. The longitudinal axis of the pipe portion also forms an obtuse angle with a portion of the longitudinal axis of the expandable elastic portion that passes through the leading end of the expandable elastic portion.

The improved instrument may be used in a method for minimizing constrictions in a vessel having a longitudinal axis in a joint area comprising the steps of: (1) providing the improved surgical instrument, (2) cutting a stab incision in the vessel; (3) first inserting the leading end of the expandable elastic portion through the incision into the interior of the vessel, (4) then inserting the trailing end of the expandable elastic portion into the vessel, (5) pressurizing the expandable elastic portion by introducing a pressure medium through the flexible pipe portion and into the expandable elastic portion so as to expand the expandable elastic portion and thereby substantially uniformly expand a portion of the vessel in the joint area, wherein the pressurizing step expands the vessel to provide additional surface area of vessel material; (6) depressurizing the expandable elastic portion by removing the pressure medium from the expandable elastic portion, allowing the expandable elastic portion to return to its unexpanded state; and (7) removing the expandable elastic portion of the member from the vessel.

BRIEF DESCRIPTION OF THE DRAWINGS

The present invention will be further described with reference to the accompanying drawing wherein like reference numerals refer to like parts in the several views, and wherein.

FIG. I is a side elevation of a T-shaped instrument of this invention, illustrating an unexpanded upper part.

Figure 4:
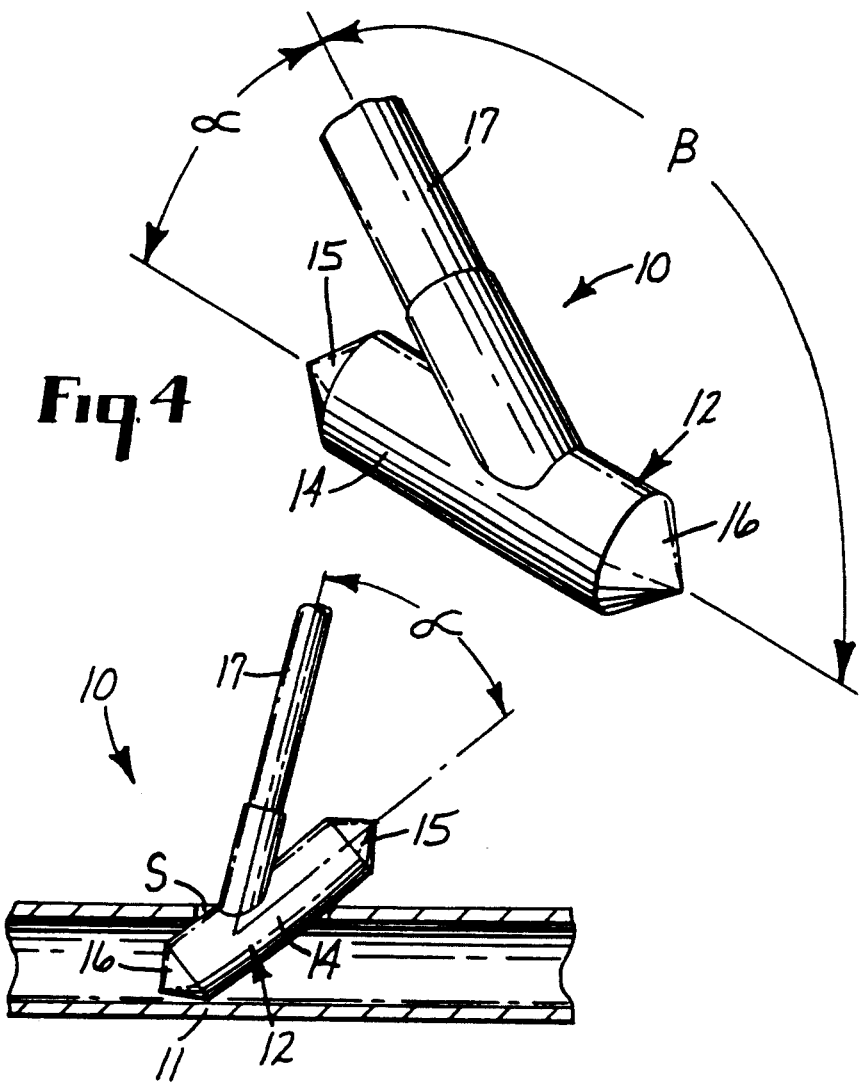
FIG. 4 is a perspective view of a second embodiment of instrument according to the present invention illustrating an unexpanded expandable elastic portion.
Figure 5:
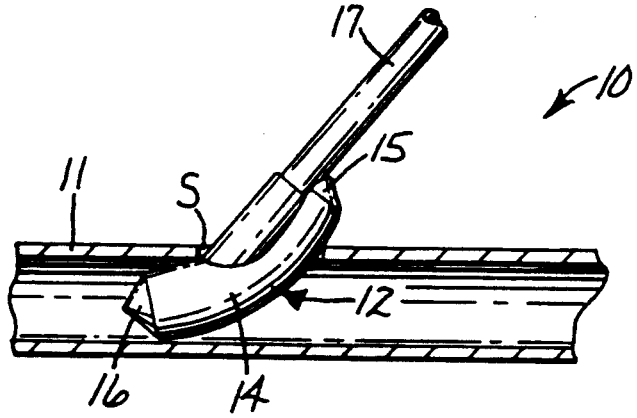
Figure 6:
Figure 7:
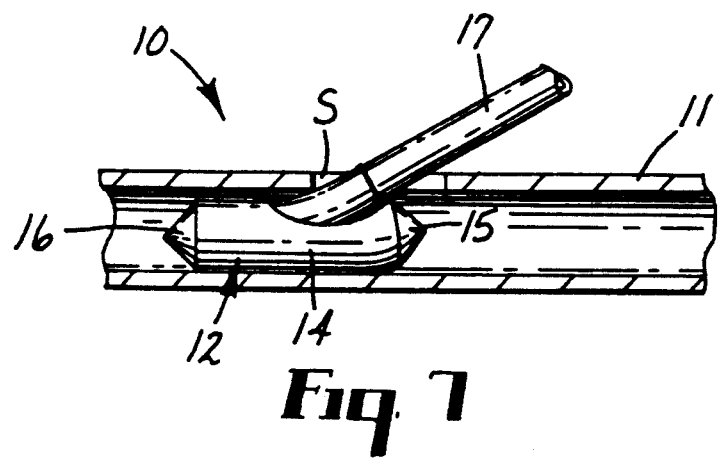
Figure 8:
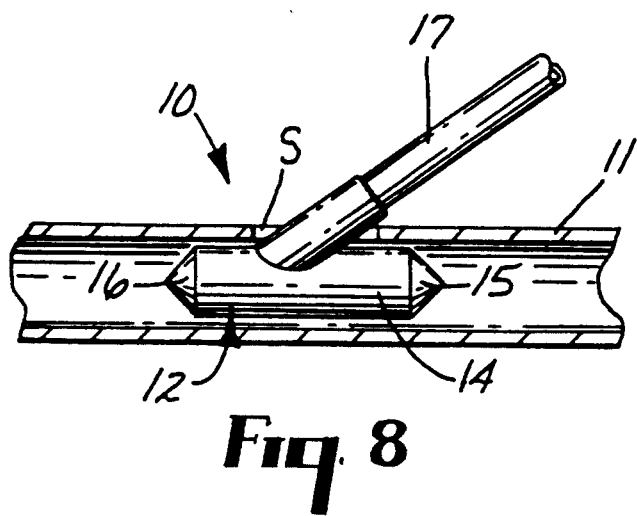
Figure 9:
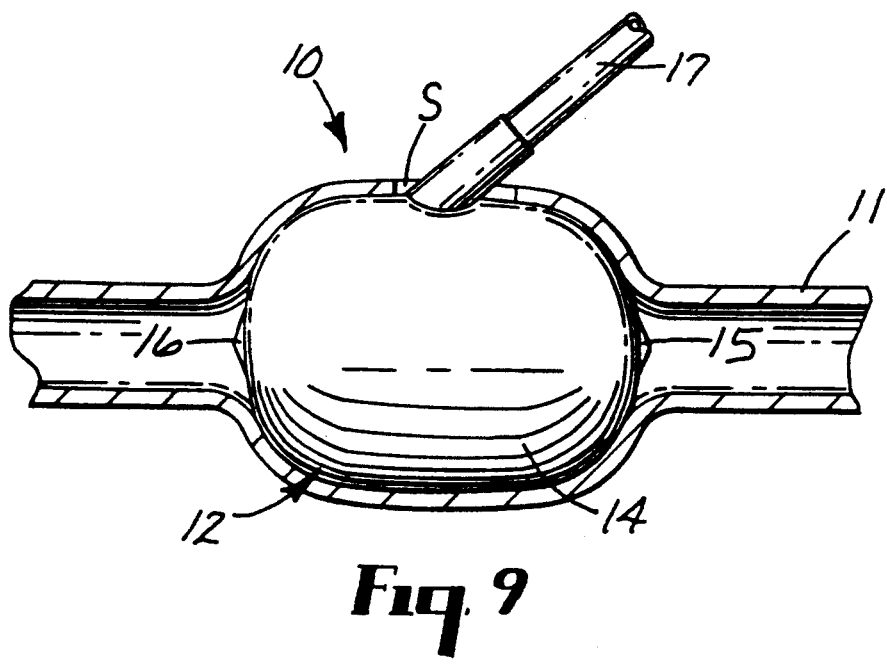

FIG.'s 5 through 8 sequentially illustrate insertion of the surgical instrument of FIG. 4 through an incision in a vessel into the interior of a vessel, wherein:

FIG. 5 is a side elevation view of the instrument of FIG. 4 illustrating a leading end of the instrument being initially inserted through an incision in a vessel;

FIG. 6 is another side view of the instrument of FIG. 4 illustrating how a trailing end of the expandable portion is deformed by contact with the flexible pipe portion;

FIG. 7 is another side view illustrating how the expandable portion is deformed while being inserted through the incision in the vessel wall;

FIG. 8 is another side view which illustrates the instrument in a retracted position with the instrument extending through the incision in the vessel wall and the expandable portion fully contained within the vessel; and FIG. 9 is yet another side view of the instrument of FIG. 4 illustrating how the expandable portion may be deformed by a pressure medium resulting in an expanded state.

DETAILED DESCRIPTION OF THE INVENTION

In accordance with this invention, a T-shaped instrument is provided having an elastically expansible upper part that includes a piece of a thin-walled hose, and a vertical part which can include another hose connected to a pressure source. The pressure source can conveniently be supplied by a common injection syringe. By pressurizing the elastic upper part of the T-shaped instrument, the upper part can be expanded to stretch the vessel wall, and by evacuating the upper part, it can be made very thin and easier to handle.

The two branches of the upper part of the T-shaped instrument can be inserted longitudinally within the vessel through a small cut or incision at the site of branching in the vessel. Once inserted, the upper part of the instrument is preferably expanded and the vessel can be expanded to about twice its original diameter. The pressure medium in the upper part of the instrument can then be evacuated to permit facilitated removal of the instrument from the vessel prior to applying anastomotic rings. The vessel can then, for example, be joined to the end of a second vessel to provide end-to-side anastomosis.

Since the vessel stretched with the T-shaped instrument of this invention is not entirely elastic, it will retain its expansion for a sufficient time for minimizing constrictions during the application of anastomotic rings. Moreover, tests have demonstrated that the uniform stress created by the upper part of the T-shaped instrument minimizes the incidence of rupturing or tearing of the incision in the vessel during expansion. This represents a benefit over other attempts to expand the vessel by means of pincettes, or the like.

Figures 1, 2:
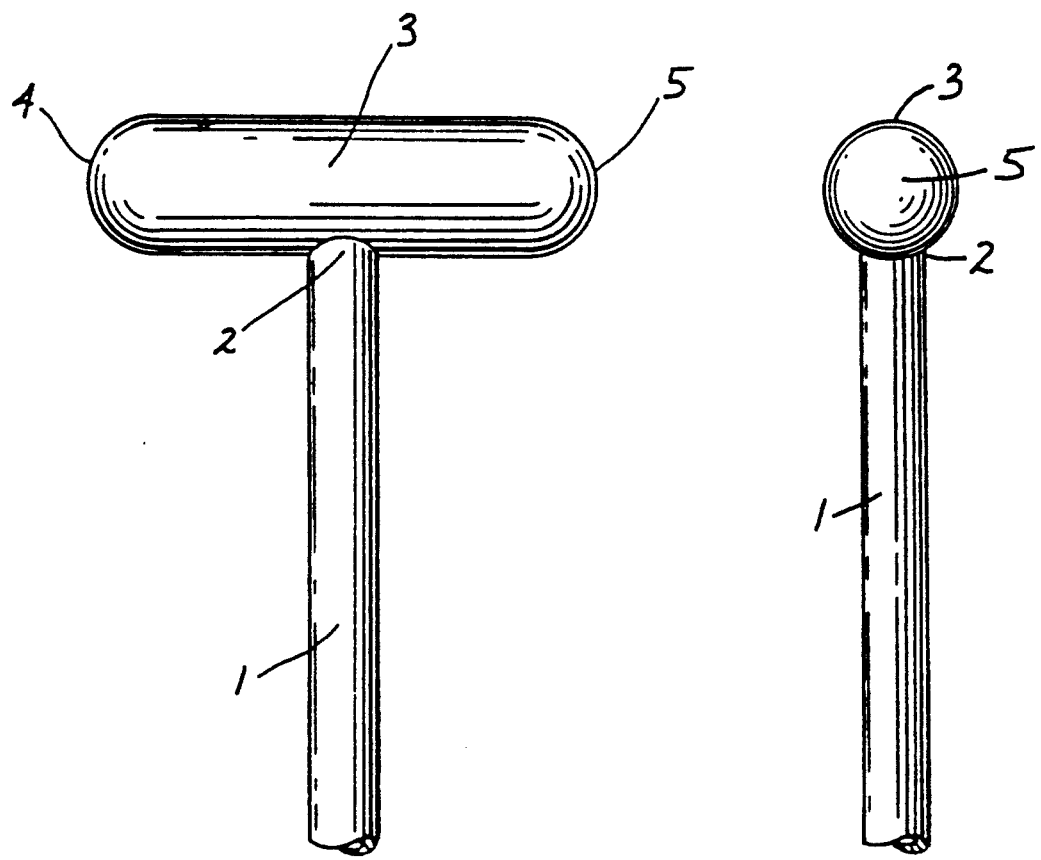
FIG. 2 is a end view of the T-shaped instrument of FIG. 1.

With reference to FIG. 1, there is shown a preferred embodiment in accordance with this invention. The instrument shown in FIG. I includes a thick-walled connection hose i of plastic, which has been welded to a side opening 2 in a thin-walled elastic plastic hose 3. The hose 3 includes end portions 4 and 5 which can be welded together. The hose 1 is very thin and preferably includes a diameter that fits on a tip of an injection syringe.

Figure 3:
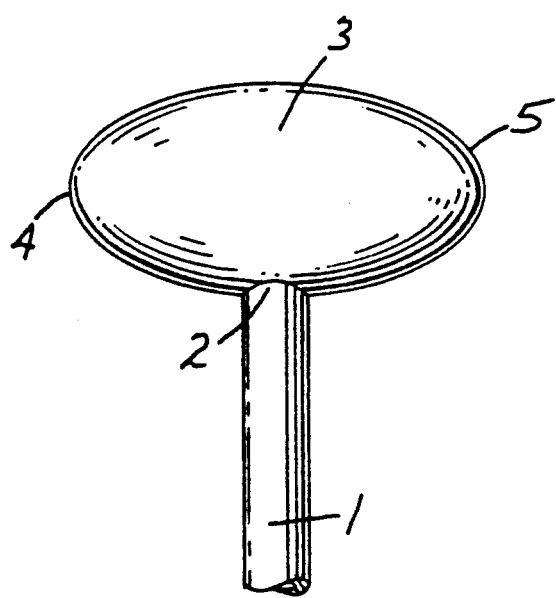
FIG. 3 illustrates another side view of the T-shaped instrument of FIG. 1, illustrating how the upper part can be subjected to a pressure medium resulting in an expanded state.

In FIG. 3, the instrument has been subjected to a pressure medium from the syringe or other source. As illustrated, the thin-walled upper part 3 of the instrument has been expanded.

Although the figures show the instrument in large detail, the diameter of the connection hose I is preferably about 1 mm, and the upper part 3 also referred to as the "balloon part" has a preferred diameter of about 2 mm and a preferred length of about 8 mm in the unaffected or unpressurized state.

From the foregoing, it has been demonstrated that this invention provides a very hygienic and economic surgical instrument for expanding blood vessels at the site of anastomotic ring placement.

A second embodiment of the present invention is described in FIGS. 4 through 9. The improved, easily insertable instrument 10 is adapted for use in a procedure for minimizing constrictions in a vessel 11 in a joint area at the site of anastomotic ring placement.

The instrument 10 according to the second embodiment of the present invention comprises an expandable elastic portion 12 or "balloon part" 12 having a middle part 14, leading 16 and trailing 15 closed ends and a longitudinal axis (see FIG.'s 4 and 5) passing through the leading 16 and trailing 15 ends. The instrument 10 also includes a flexible pipe portion 17 joined to and in open communication with the elastic portion 12 generally at the middle part 14. The pipe portion 12 has a longitudinal axis forming an acute angle (Alpha, see FIG.'s 4 and 5) with a portion of the longitudinal axis of the expandable elastic portion 12 that passes through the trailing end 15 of the expandable elastic portion 12. The longitudinal axis of the pipe portion 17 also forms an obtuse angle (Beta, see FIG. 4) with a portion of the longitudinal axis of the expandable elastic portion 12 that passes through the leading end 16 of the expandable elastic portion 12. A distal end (not shown) of the pipe portion 17 is adapted to engage an injection syringe.

For example, the expandable elastic portion 12 may be constructed from a thin wall molded piece with a preferred diameter in an unexpanded state of about 2 millimeters outside diameter, a diameter in an expanded state of approximately 4 millimeters, a wall thickness of about 0.2 millimeters and a preferred length of 8 millimeters in the unexpanded state. The ends 15 and 17 may be any suitable shape such as conical, frustoconical, arcuate or combinations thereof.

Flexible pipe portion 17 may be constructed from a relatively thick-walled plastic hose and have an inner diameter of about 0.6 millimeters and an outer diameter of about 1.2 millimeters. The flexible pipe portion 17 and the expandable elastic portion 12 may be joined using any conventional method such as, but not limited to adhesive bonding and welding. Preferably, the elastic portion 12 is more elastic than the pipe portion 17.

The acute angle Alpha is between approximately twenty-five (25) and fifty-five (55) degrees, and is preferably approximately forty (40) degrees. Generally, if the acute angle Alpha is less than approximately twenty-five (25) degrees, then the flexible hose 17 tends to interfere with the insertion of the trailing end 15 of the instrument 10 into the vessel 11. If the acute angle Alpha is more than approximately fifty-five (55) degrees, then the instrument suffers from the attendant insertion difficulties associated with the T-shaped instrument shown in FIG. 1 and the benefits associated with the instrument 10 are attenuated.

The expandable elastic portion 12 is adapted to be expanded between an unexpanded state (FIG.'s 4 and 5) with the expandable elastic portion 12 being generally cylindrically shaped and an expanded state (FIG. 9) with at least the middle part 14 spaced from its unexpanded position.

Unlike the instrument shown in FIGS. 1 through 3, the structure of the instrument 10 affords its use in a method for minimizing constrictions in a vessel 11 having a longitudinal axis in a joint area comprising the steps of: (1) providing an instrument 10 comprising an expandable elastic portion 12 having a middle part 14, leading 16 and trailing 15 closed ends and a longitudinal axis passing through the leading 16 and trailing 15 ends, and a flexible pipe portion 17 joined to and in open communication with the elastic portion 12 generally at the middle part 14, the pipe portion 17 having a longitudinal axis forming an acute angle (Alpha) with a portion of the longitudinal axis of the expandable elastic portion 12 that passes through the trailing end 15 of the expandable elastic portion 12 and forming an obtuse angle (Beta) with a portion of the longitudinal axis of the expandable elastic portion 12 that passes through the leading end 16 of the expandable elastic portion 12, (2) cutting a longitudinal stab incision S in the vessel 11 at the site of branching in the vessel 11; (3) first inserting the end 16 of the expandable elastic portion 12 through the incision S into the interior of the vessel 11 (e.g. FIG. 5), (4) then inserting the trailing end 15 of the expandable elastic portion 12 into the vessel 11, (5) pressurizing (FIG. 9) the expandable elastic portion 12 by introducing a pressure medium through said flexible pipe portion 17 and into the expandable elastic portion 12 so as to expand the expandable elastic portion 12 and thereby substantially uniformly expand a portion of the vessel 11 in the joint area, wherein the pressurizing step expands the vessel 11 to provide additional surface area of vessel material; (6) depressurizing the expandable elastic portion 12 by removing the pressure medium from the expandable elastic portion 12, allowing the expandable elastic portion 12 to return to its unexpanded state; and (7) removing the expandable elastic portion 12 of the instrument 10 from the vessel 11.

Initially inserting the leading end 16 of the expandable elastic portion 12 through the incision S into the interior of the vessel 11 is believed to promote ease of insertion of the instrument into the vessel by providing increased user control. Also, initially inserting the end 16 of the expandable elastic portion 12 through the incision S into the interior of the vessel 11 is believed to reduce the likelihood of unduly enlarging the incision S during the surgical procedure.

FIG.'s 5 through 8 sequentially illustrate insertion of the surgical instrument 10 through an incision S in a vessel 11 into the interior of the vessel 11. Generally, just before insertion of the instrument 10 into the vessel 11, the elastic portion 12 may be slightly filled with a pressure medium to impart rigidity to the elastic portion 12. The leading end 16 is readily fed into the interior of the vessel 11 through incision S and is moved into the vessel until the trailing end 15 is situated within the vessel 11.

FIG. 5 illustrates the instrument 10 being initially inserted into the incision S. FIG. 6 illustrates the expandable portion 12 deforming while being inserted through the incision in the vessel wall causing the trailing end 15 to collapse and follow the leading end into the interior of the vessel. The expandable elastic portion 12 is pliable and resilient which allows the trailing end 15 to deform and collapse against the pipe 17 while being inserted through the stab incision S in the vessel wall, yet allows it to return to its preinsertion shape when trailing end 17 passes through incision S and is enclosed within the vessel 11.

FIG. 6 illustrates how a trailing end 15 of the expandable portion 12 is deformed by contact with the flexible pipe portion 17. The instrument is then retracted until the tube 17 is protruding through the incision S in the vessel wall and both the leading and trailing ends of the expandable elastic portion are contained within the vessel 11. FIG. 8 illustrates the instrument 10 in a retracted condition with the tube 17 extending through the incision S in the vessel wall and the expandable portion 12 fully contained within the vessel.

Once the elastic portion 12 is inserted, step (5) above may be performed by connecting the hose 17 to a common injection syringe. By pressurizing the elastic portion 12, the elastic portion 12 may be expanded to stretch the vessel wall 11, and by evacuating the elastic portion 12, it can be rendered very thin and easy to maneuver to thereby facilitate removal of the instrument 10 prior to the application of anastomostic rings. The vessel can then, for example, be joined to the end of a second vessel to provide end-to-side anastomosis.

FIG. 9 is yet another side view of the instrument of FIG. 4 illustrating how the expandable portion may be deformed by a pressure medium resulting in an expanded state. Since the vessel 11 stretched with the instrument 10 is not entirely elastic, it will retain its expansion for a sufficient time or minimizing constrictions during the application of anastomostic rings.

The present invention has now been described with reference to several embodiments thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

What is claimed is:

1. A method for minimizing constrictions in a vessel having a longitudinal axis in a joint area comprising the steps of:

providing an instrument comprising an expandable elastic portion having a middle part, leading and trailing closed ends and a longitudinal axis passing through the leading and trailing ends, and a flexible pipe portion joined to and in open communication with the elastic portion generally at the middle part, the pipe portion having a longitudinal axis forming an acute angle with a portion of the longitudinal axis of the expandable elastic portion that passes through the trailing end of the expandable elastic portion and forming an obtuse angle with a portion of the longitudinal axis of the expandable elastic portion that passes through the leading end of the expandable elastic portion, the elastic portion being more elastic than the pipe portion;

cutting a stab incision in the vessel;

first inserting the leading end of the expandable elastic portion through the incision into the interior of the vessel, then inserting the trailing end of the expandable elastic portion into the vessel, pressurizing the expandable elastic portion by introducing a pressure medium through said flexible pipe portion and into the expandable elastic portion so as to expand the expandable elastic portion and thereby substantially uniformly expand a portion of the vessel in said joint area, wherein said pressurizing step expands said vessel to provide additional surface area of vessel material; and depressurizing the expandable elastic portion by removing the pressure medium from the expandable elastic portion, allowing the expandable elastic portion to return to its unexpanded state; and removing the expandable elastic portion of the instrument from said vessel.

2. A method according to claim 1, wherein the step of depressurization comprises evacuating the expandable elastic portion causing the expandable elastic portion to collapse to a size smaller than its original unexpanded state.

3. A method according to claim 1, wherein the pressure medium is provided to the member by means of a syringe attached to a distal end of the instrument.

4. A method according to claim 1, wherein the expandable elastic portion of the member is approximately 2 millimeters in diameter and approximately 8 millimeters in length.

5. A method according to claim 1, wherein the step of first inserting the leading end of the expandable elastic portion through the incision into the interior of the vessel, comprises moving the instrument toward the interior of the vessel.

6. A method according to claim 1 wherein the step of then inserting the trailing end of the expandable elastic portion into the vessel comprises causing the trailing end to collapse and follow the leading end into the interior of the vessel.

* * * * *